United States Patent
Wu et al.

(10) Patent No.: US 12,280,369 B2
(45) Date of Patent: *Apr. 22, 2025

(54) DETECTION CHIP, USING METHOD FOR THE SAME, AND REACTION SYSTEM

(71) Applicants: BEIJING BOE TECHNOLOGY DEVELOPMENT CO., LTD., Beijing (CN); BOE TECHNOLOGY GROUP CO., LTD., Beijing (CN)

(72) Inventors: Zhihong Wu, Beijing (CN); Zijian Zhao, Beijing (CN); Yudan Yin, Beijing (CN); Mengjun Hou, Beijing (CN); Kang Peng, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 121 days.

This patent is subject to a terminal disclaimer.

(21) Appl. No.: 18/112,671

(22) Filed: Feb. 22, 2023

(65) Prior Publication Data
US 2023/0191394 A1    Jun. 22, 2023

Related U.S. Application Data

(63) Continuation of application No. 16/634,309, filed as application No. PCT/CN2019/080625 on Mar. 29, 2019, now Pat. No. 11,607,682.

(30) Foreign Application Priority Data

Jan. 15, 2019   (WO) .................. PCT/CN2019/071803

(51) Int. Cl.
*B01L 3/00*      (2006.01)
*C12Q 1/686*     (2018.01)
*G01N 21/64*     (2006.01)

(52) U.S. Cl.
CPC ...... *B01L 3/5023* (2013.01); *B01L 2300/0645* (2013.01); *B01L 2300/1811* (2013.01); *C12Q 1/686* (2013.01); *G01N 21/6428* (2013.01)

(58) Field of Classification Search
None
See application file for complete search history.

(56) References Cited

U.S. PATENT DOCUMENTS

2004/0028566 A1   2/2004   Ko et al.
2005/0230252 A1   10/2005  Tsai et al.
(Continued)

FOREIGN PATENT DOCUMENTS

CN   1267089 A   9/2000
CN   1460723 A   12/2003
(Continued)

OTHER PUBLICATIONS

First Chinese Office Action from Chinese Patent Application No. 201980000439.5 dated Mar. 14, 2022.
(Continued)

*Primary Examiner* — Xiaoyun R Xu
(74) *Attorney, Agent, or Firm* — Dilworth & Barrese, LLP.; Michael J. Musella, Esq.

(57) ABSTRACT

A detection chip, a using method for the same, and a reaction system. The detection chip includes a first substrate, a micro-cavity defining layer, and a heating electrode. The micro-cavity defining layer is on the first substrate and defines a plurality of micro-reaction chambers. The heating electrode is on the first substrate and is closer to the first substrate than the micro-cavity defining layer, and is configured to heat a plurality of micro-reaction chambers. The orthographic projection of the plurality of micro-reaction chambers on the first substrate is within the orthographic projection of the heating electrode on the first substrate.

18 Claims, 9 Drawing Sheets

(56) References Cited

U.S. PATENT DOCUMENTS

| | | |
|---|---|---|
| 2006/0000709 A1 | 1/2006 | Bohm et al. |
| 2012/0100551 A1 | 4/2012 | Kojima et al. |
| 2012/0308449 A1 | 12/2012 | Yang et al. |
| 2017/0368526 A1 | 12/2017 | Choi et al. |
| 2018/0126381 A1 | 5/2018 | Huff et al. |

FOREIGN PATENT DOCUMENTS

| | | | |
|---|---|---|---|
| CN | 1715930 | A | 1/2006 |
| CN | 1922478 | A | 2/2007 |
| CN | 201732093 | U | 2/2011 |
| CN | 102071136 | A | 5/2011 |
| CN | 102899245 | A | 1/2013 |
| CN | 104588137 | A | 5/2015 |
| CN | 106501520 | A | 3/2017 |
| CN | 107475074 | A | 12/2017 |
| CN | 107983426 | A | 5/2018 |
| CN | 108660068 | A | 10/2018 |
| CN | 108816300 | A | 11/2018 |
| KR | 1020140067421 | A | 6/2014 |
| KR | 101443074 | B1 | 9/2014 |
| WO | 2017127570 | A1 | 7/2017 |
| WO | 2018183723 | A1 | 10/2018 |

OTHER PUBLICATIONS

Non-Final Office Action from U.S. Appl. No. 16/753,115 dated Apr. 1, 2022.

First Chinese Office Action from Chinese Patent Application No. 201980000441.2 dated Jul. 30, 2021.

Extended European Search Report for Application No. 19858704.0 dated Sep. 9, 2022.

Non-final Office Action from U.S. Appl. No. 16/634,309 dated Jan. 24, 2022.

Final Office Action from U.S. Appl. No. 16/634,309 dated Jun. 29, 2022.

International Search Report for International Application No. PCT/CN2019/071803 dated Sep. 26, 2019.

International Search Report for International Application No. PCT/CN2019/080625 dated Oct. 15, 2019.

Supplementary European Search Report for Application No. 19861273.1 dated Nov. 28, 2022.

International Search Report for International Application No. PCT/CN2019/080626 dated Jan. 2, 2020.

Second Japanese Office Action from Japanese Patent Application No. 2021-504490 Dated Mar. 20, 2023.

Water Droplet | average contact angle: 72.92°
left contact angle: 74.01°
right contact angle: 73.83°
volume of water droplet: 4.45µL

DETECTION CHIP, USING METHOD FOR THE SAME, AND REACTION SYSTEM

CROSS REFERENCE TO RELATED APPLICATIONS

The present application is a continuation application of and claims priority of a prior application U.S. Ser. No. 16/634,309, filed on Jan. 27, 2020, which is the National Stage of PCT/CN2019/080625 filed on Mar. 29, 2019, and claims priority of PCT International Application No. PCT/CN2019/071803, filed on Jan. 15, 2019, the disclosure of which are incorporated herein by reference in its entirety as part of the present application.

TECHNICAL FIELD

Embodiments of the present disclosure relate to a detection chip, a using method for the same, and a reaction system.

BACKGROUND

Polymerase chain reaction (Polymerase Chain Reaction, PCR) is a molecular biology technique for amplifying specific DNA fragments, which can replicate a small amount of deoxyribonucleic acid (DNA) multiple times to increase the amount of DNA significantly. Different from the traditional PCR technology, the digital polymerase chain reaction (digital PCR, dPCR) chip technology is to fully dilute the nucleic acid sample so that the number of target molecules (i.e., DNA templates) in each reaction unit is less than or equal to 1, perform PCR amplification on the target molecules in each reaction unit, and statistically analyze the fluorescence signal of each reaction unit after the amplification is completed, so as to realize the absolute quantitative detection of single molecule DNA. The dPCR is widely applied to clinical diagnoses, genetic instability analyses, single-cell gene expression, environmental microorganism detection, and prenatal diagnoses due to the advantages of high sensitivity, strong specificity, high detection throughput, and high quantitative accuracy.

SUMMARY

At least some embodiments of the present disclosure provide a detection chip, which includes: a first substrate; a micro-cavity defining layer, being on the first substrate and defining a plurality of micro-reaction chambers; and a heating electrode, being on the first substrate and closer to the first substrate than the micro-cavity defining layer, and configured to heat the plurality of micro-reaction chambers, wherein an orthographic projection of the plurality of micro-reaction chambers on the first substrate is within an orthographic projection of the heating electrode on the first substrate.

For example, in the detection chip provided by some embodiments of the present disclosure, each of the plurality of micro-reaction chambers comprises a reaction well, and the reaction well comprises a sidewall and a bottom.

For example, in the detection chip provided by some embodiments of the present disclosure, the plurality of micro-reaction chambers are arranged in an array on the first substrate.

For example, the detection chip provided by some embodiments of the present disclosure further comprises a hydrophilic layer, wherein the hydrophilic layer covers the sidewall and the bottom of each of the plurality of micro-reaction chambers.

For example, in the detection chip provided by some embodiments of the present disclosure, the hydrophilic layer further covers a surface of the micro-cavity defining layer away from the first substrate.

For example, the detection chip provided by some embodiments of the present disclosure further comprises: a second substrate disposed opposite to the first substrate; and a hydrophobic layer, being on a side of the second substrate facing the first substrate; wherein the micro-cavity defining layer is on a side of the first substrate facing the second substrate.

For example, the detection chip provided by some embodiments of the present disclosure further comprises a control electrode, wherein the control electrode is on the first substrate and is electrically connected with the heating electrode through a via or overlaps with the heating electrode, and the control electrode is configured to apply an electrical signal to the heating electrode.

For example, the detection chip provided by some embodiments of the present disclosure further comprises a first insulating layer, wherein the first insulating layer covers the control electrode, the heating electrode is on the first insulating layer, the first insulating layer comprises the via penetrating the first insulating layer, and the heating electrode is electrically connected to the control electrode through the via.

For example, the detection chip provided by some embodiments of the present disclosure further comprises a second insulating layer, wherein the second insulating layer is between the heating electrode and the micro-cavity defining layer.

For example, in the detection chip provided by some embodiments of the present disclosure, the first substrate comprises a reaction region and a peripheral region, the peripheral region at least partially surrounds the reaction region, the reaction region comprises a functional region, the micro-cavity defining layer is in the functional region, the control electrode and the via are in the peripheral region, and the heating electrode is in the reaction region and the peripheral region.

For example, the detection chip provided by some embodiments of the present disclosure further comprises a plurality of spacers, wherein the plurality of spacers are in the peripheral region and between the first substrate and the second substrate, and the plurality of spacers are configured to maintain a distance between the first substrate and the second substrate.

For example, in the detection chip provided by some embodiments of the present disclosure, a height of the spacer is greater than a height of the micro-cavity defining layer in a direction perpendicular to the first substrate.

For example, the detection chip provided by some embodiments of the present disclosure further comprises a sample inlet and a sample outlet, wherein the reaction region further comprises a non-functional region, the sample inlet and the sample outlet are in the non-functional region and on different sides of the functional region, and the sample inlet and the sample outlet penetrate the second substrate and the hydrophobic layer.

For example, in the detection chip provided by some embodiments of the present disclosure, the first substrate and the second substrate are glass substrates.

For example, in the detection chip provided by some embodiments of the present disclosure, a material of the hydrophilic layer comprises silicon oxide, and a material of the hydrophobic layer comprises resin or silicon nitride.

For example, in the detection chip provided by some embodiments of the present disclosure, a material of the micro-cavity defining layer comprises a photoresist.

For example, in the detection chip provided by some embodiments of the present disclosure, a shape of each of the plurality of micro-reaction chambers is a cylinder, a diameter of a bottom of the cylinder ranges from 1 micron to 100 microns, and a height of the cylinder ranges from 5 microns to 100 microns.

For example, the detection chip provided by some embodiments of the present disclosure further comprises a first temperature sensor, wherein the first temperature sensor is on a side of the first substrate away from the micro-cavity defining layer, and the first temperature sensor is in the reaction region and is configured to detect a temperature of the reaction region.

At least some embodiments of the present disclosure further provide a reaction system reaction system comprising a control device and the detection chip according to any one of the embodiments of the present disclosure, wherein the control device is electrically connected to the detection chip, and is configured to apply an electrical signal to the detection chip to drive the heating electrode of the detection chip.

For example, the reaction system provided by some embodiments of the present disclosure further comprises a second temperature sensor, wherein the second temperature sensor is on a side of the first substrate of the detection chip away from the micro-cavity defining layer, the second temperature sensor is in the reaction region of the first substrate, and the second temperature sensor is configured to detect a temperature of the reaction region of the detection chip.

At least some embodiments of the present disclosure also provide a using method of the detection chip according to any one of the embodiments of the present disclosure comprising: causing a reaction system solution to enter a plurality of micro-reaction chambers of the detection chip through an sample inlet of the detection chip; and applying an electrical signal to a control electrode of the detection chip to drive, by the control electrode, the heating electrode to heat the plurality of micro-reaction chambers.

For example, the using method provided by some embodiments of the present disclosure further comprises cooling the plurality of micro-reaction chambers to change a temperature of the plurality of micro-reaction chambers, so that the reaction system solution in the plurality of micro-reaction chambers undergoes a temperature cyclic process comprising a denaturation stage, an annealing stage and an extension stage.

For example, the using method provided by some embodiments of the present disclosure further comprises performing optical detection on the detection chip to obtain a fluorescent image.

BRIEF DESCRIPTION OF THE DRAWINGS

In order to clearly illustrate the technical solution of the embodiments of the present disclosure, the drawings of the embodiments will be briefly described in the following; it is obvious that the described drawings are only related to some embodiments of the present disclosure and thus are not limitative of the present disclosure.

DETAILED DESCRIPTION

Figure 1:
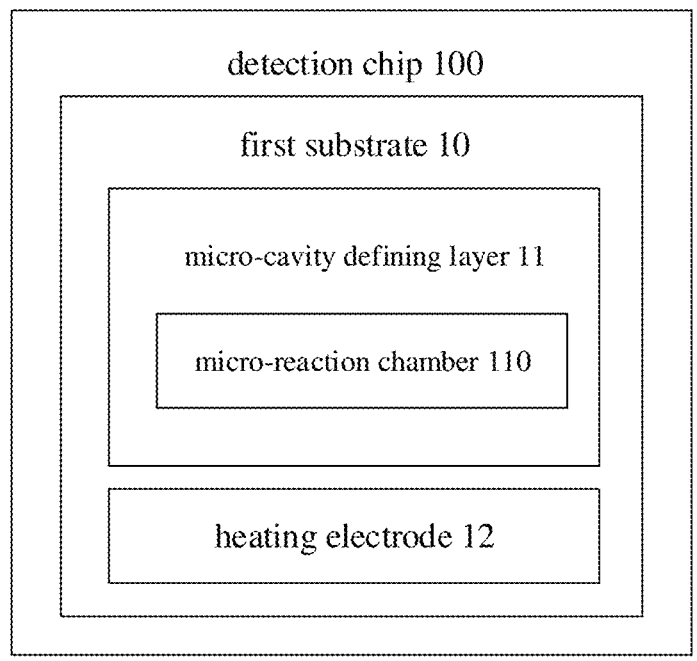
FIG. 1 is a schematic block diagram of a detection chip provided by some embodiments of the present disclosure.

In order to make objects, technical details and advantages of the embodiments of the present disclosure apparent, the technical solutions of the embodiments will be described in a clearly and fully understandable way in connection with the drawings related to the embodiments of the present disclosure. Apparently, the described embodiments are just a part but not all of the embodiments of the present disclosure. Based on the described embodiments herein, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present invention belongs. The terms "first," "second," etc., which are used in the description and the claims of the present application for invention, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

During the PCR reaction, the double-stranded structure of the DNA fragment is denatured to form a single-stranded structure at high temperatures, the primers and the single strands are bound according to the principle of complementary base pairing at low temperatures, and base binding extension is achieved at the optimal temperature for the DNA polymerase. The above process is a temperature cyclic process of denaturation-annealing-extension. Through numerous temperature cyclic processes of denaturation-annealing-extension, DNA fragments can be replicated in large numbers.

In order to achieve the above temperature cyclic process, a series of external equipment is usually required to heat and cool the detection chip, which makes the equipment bulky, complicated to operate, and costly. In addition, in the process of heating and cooling the detection chip, the overall temperature of the detection chip changes accordingly, so that the temperature of structures and components in the detection chip other than the micro-cavity containing the DNA fragments also changes, thereby increasing the risk of damaging components such as circuits. Generally, dPCR products are mostly processed on silicon or need to cooperate with a droplet preparation system, which makes the detection chip costly and complicated to process.

At least one embodiment of the present disclosure provides a detection chip, a using method of the detection chip, and a reaction system. By providing a heating electrode in the detection chip, the temperature of the micro-reaction chamber of the detection chip can be effectively controlled, so that the temperature cyclic process can be realized without driving the droplets and without external heating equipment, thereby resulting in a high integration degree, simplicity of operation, low production costs, and high efficiency of sample input.

Hereinafter, embodiments of the present disclosure will be described in detail with reference to the accompanying drawings. It should be noted that the same reference numerals in the various drawings indicate the same elements that have been described.

At least one embodiment of the present disclosure provides a detection chip including a first substrate, a micro-cavity defining layer, and a heating electrode. The micro-cavity defining layer is located on the first substrate and defines a plurality of micro-reaction chambers. The heating electrode is located on the first substrate and is closer to the first substrate than the micro-cavity defining layer, and is configured to heat the plurality of micro-reaction chambers. The orthographic projections of the plurality of micro-reaction chambers on the first substrate are located within the orthographic projection of the heating electrode on the first substrate.

Figure 2:
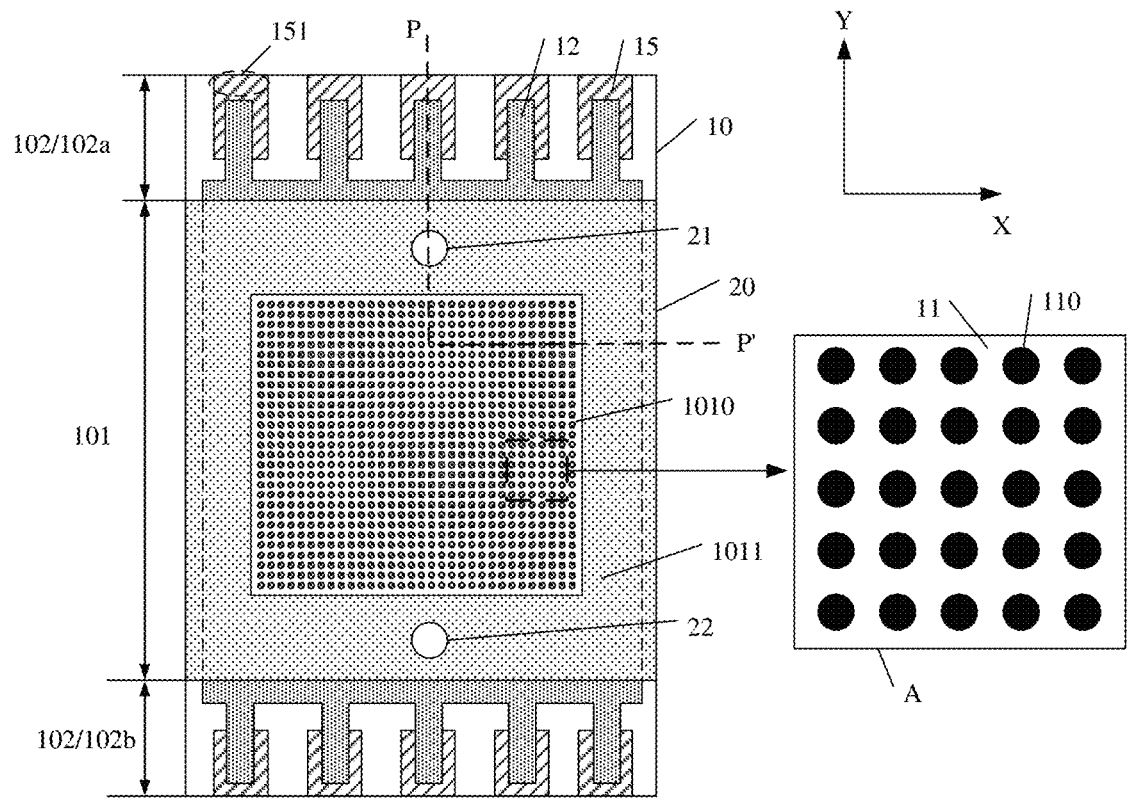
FIG. 2 is a schematic plane view of a detection chip provided by some embodiments of the present disclosure.
Figure 3:
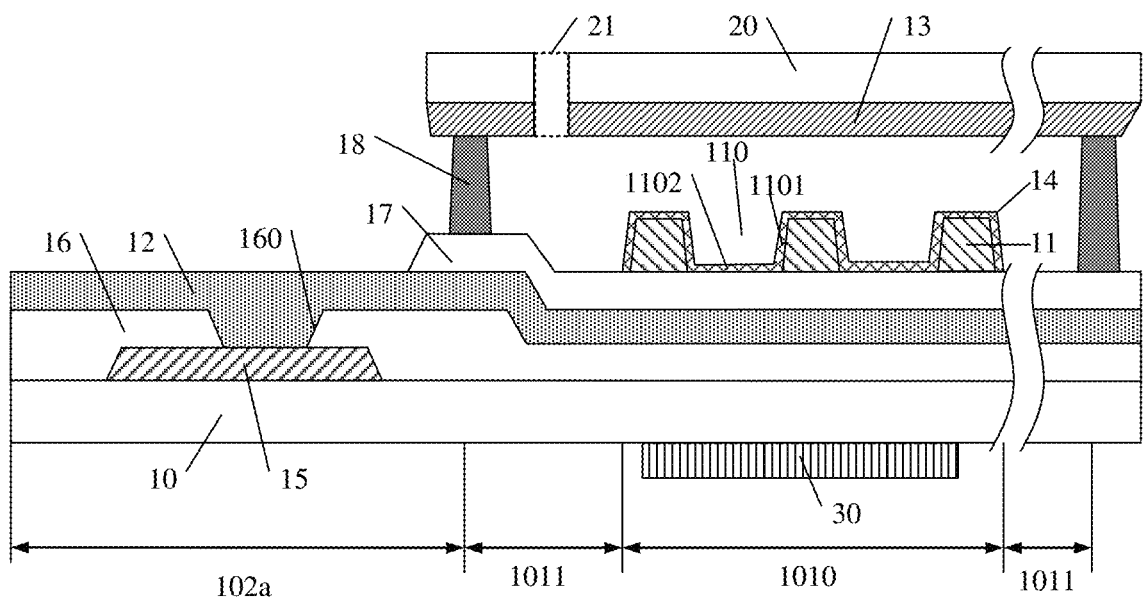
FIG. 3 is a partial cross-sectional structural diagram of a detection chip provided by some embodiments of the present disclosure.

FIG. 1 is a schematic block diagram of a detection chip provided by some embodiments of the present disclosure, FIG. 2 is a schematic plane view of a detection chip provided by some embodiments of the present disclosure, and FIG. 3 is a partial cross-sectional structural diagram of a detection chip provided by some embodiments of the present disclosure. For example, FIG. 3 is a cross-sectional view taken along a line P-P' in FIG. 2.

For example, as shown in FIG. 1, a detection chip 100 includes a first substrate 10, a micro-cavity defining layer 11, and a heating electrode 12. The first substrate 10 plays a role of protecting, support, and the like. Both the micro-cavity defining layer 11 and the heating electrode 12 are located on the first substrate 10. The micro-cavity defining layer 11 defines a plurality of micro-reaction chambers 110. The heating electrode 12 is closer to the first substrate 10 than the micro-cavity defining layer 11, and is configured to heat the plurality of micro-reaction chambers 110. The orthographic projections of the plurality of micro-reaction chambers 110 on the first substrate 10 are located within the orthographic projection of the heating electrode 12 on the first substrate 10. For example, the detection chip 100 may be used for a polymerase chain reaction (e.g., a digital polymerase chain reaction), and may be further used for a detection process after the reaction.

For example, as shown in FIG. 2 and FIG. 3, the heating electrode 12 is located on the first substrate 10, and the heating electrode 12 can receive an electrical signal (e.g., a voltage signal), so that when there is a current flowing through the heating electrode 12, heat is generated and conducted to at least a portion of the micro-reaction chamber 110 for the polymerase chain reaction. For example, the heating electrode 12 may be made of an electrically conductive material with a large electrical resistivity, so that the heating electrode 12 generates a large amount of heat when a small electrical signal is provided, so as to improve the energy conversion rate. The heating electrode 12 may be made of, for example, a transparent conductive material, for example, indium tin oxide (ITO), tin oxide, or the like, and may also be made of other suitable materials, such as metal, which is not limited in the embodiments of the present disclosure. For example, the heating electrode 12 is a planar electrode, for example, the heating electrode 12 is uniformly formed on the first substrate 10 by using a conductive material, so that the plurality of micro-reaction chambers 110 are uniformly heated. Certainly, the embodiments of the present disclosure are not limited thereto, and the heating electrode 12 may also have a specific shape or pattern, such as a polygonal line shape, a circular arc shape, etc., which may be determined according to the distribution manner of the plurality of micro-reaction chambers 110.

The micro-cavity defining layer 11 is located on the first substrate 10 and is also located on the heating electrode 12, that is, the heating electrode 12 is closer to the first substrate 10 than the micro-cavity defining layer 11. The micro-cavity defining layer 11 defines the plurality of micro-reaction chambers 110, and adjacent micro-reaction chambers 110 are at least partially spaced from each other (for example, by a spacing wall). For example, each of the plurality of micro-reaction chambers 110 includes a reaction well including a sidewall 1101 and a bottom 1102. The reaction well provides an accommodating space for the reaction system solution, and droplets of the reaction system solution that enter the micro-cavity defining layer 11 and move to the reaction well will remain relatively stably in the reaction well. For example, the reaction well may be a micro-reaction groove, a micro-reaction depression, or the like, as long as the reaction well has a space to accommodate the reaction system solution, which is not limited in the embodiments of the present disclosure.

For example, the shapes of the plurality of micro-reaction chambers 110 may be the same. The three-dimensional shape of each micro-reaction chamber 110 is, for example, approximately a cylinder, that is, as shown in FIG. 3 and the partially enlarged view A of FIG. 2, a cross section in a direction perpendicular to the first substrate 10 is approximately a rectangle and a cross section in a plane parallel to the first substrate 10 is approximately a circle. For example, the diameter of the bottom of the cylinder ranges from 1 micron to 100 microns, for example, 20 microns to 50 microns. The height of the cylinder ranges from 5 microns to 100 microns, for example, 30 microns to 50 microns. For example, in some examples, the diameter of the bottom of the cylinder is 8 microns and the height of the cylinder is 9.8 microns. It should be noted that the shapes of at least part of the micro-reaction chambers 110 may be different.

The shape of the micro-reaction chamber 110 may be designed according to actual requirements. For example, the shape of each micro-reaction chamber 110 may be a circular truncated cone, a rectangular parallelepiped, a polygonal prism, a sphere, an ellipsoid, and the like, which is not limited in the embodiments of the present disclosure. For example, the cross-sectional shape of the micro-reaction chamber 110 in a plane parallel to the first substrate 10 may be an oval, a triangle, a polygon, an irregular shape, etc., and the cross-section of the micro-reaction chamber 110 in a direction perpendicular to the first substrate 10 may be a square, a circle, a parallelogram, a polygon such as a trapezoid, etc.

For example, as shown in FIG. 2, the plurality of micro-reaction chambers 110 are uniformly distributed on the first substrate 10. For example, the plurality of micro-reaction chambers 110 are arranged in an array in the first direction X and the second direction Y on the first substrate 10. In this way, the fluorescent image obtained by performing the optical detection on the detection chip 100 in a subsequent stage can be more regular and neat, so as to obtain the detection result quickly and accurately. Certainly, the embodiments of the present disclosure are not limited thereto, and the plurality of micro-reaction chambers 110 may also be unevenly distributed on the first substrate 10 or may be arranged in other manners, which is not limited in the embodiments of the present disclosure. For example, the number of the plurality of micro-reaction chambers 110 may be in a range of 2,000 to 1,000,000. For example, in some examples, the number of the plurality of micro-reaction chambers 110 is in a range of 40,000-100,000. As a result, the detection throughput of the detection chip 100 is large.

It should be noted that, in the embodiment of the present disclosure, the size and number of the micro-reaction chambers 110 may be determined according to actual requirements, and the size and number of the micro-reaction chambers 110 are related to the sizes of the detection chip 100 and the first substrate 10. In a case where the size of the micro-reaction chamber 110 is constant, the larger the number of the micro-reaction chambers 110 is, the larger the size of the detection chip 100 and the first substrate 10 are accordingly.

Because the target molecules (i.e., the DNA templates) in the reaction system solution is fully diluted, when the reaction system solution enters each micro-reaction chamber 110, the number of the target molecules (i.e., the DNA templates) in each micro-reaction chamber 110 is less than or equal to 1, that is, each micro-reaction chamber 110 includes only one target molecule or does not include the target molecule, so as to obtain accurate detection results in subsequent stages.

For example, the material of the micro-cavity defining layer 11 is a photoresist that can be processed in a thick film. The photoresist can be formed on the first substrate 10 by spin coating, and has a large thickness. For example, the thickness of the micro-cavity defining layer 11 may range from 5 microns to 100 microns, for example, 9.8 microns. For example, the micro-cavity defining layer 11 may be patterned and etched to obtain the plurality of micro-reaction chambers 110 arranged to be spaced from each other.

For example, the orthographic projections of the plurality of micro-reaction chambers 110 on the first substrate 10 are located within the orthographic projection of the heating electrode 12 on the first substrate 10. Here, the orthographic projection refers to a projection on the first substrate 10 in a direction perpendicular to the first substrate 10. For example, as shown in FIG. 2, in a direction perpendicular to the first substrate 10, the projections of the plurality of micro-reaction chambers 110 on the first substrate 10 are located within the projection of the heating electrode 12 on the first substrate 10, and the above-mentioned projection of the heating electrode 12 is larger than the above-mentioned projections of the plurality of micro-reaction chambers 110. In this way, each micro-reaction chamber 110 can be heated by the heating electrode 12. Due to the heat dissipation effect at the edge of the heating electrode 12, the working temperature at the edge of the heating electrode 12 is lower than the working temperature at the central area of the heating electrode 12. Therefore, with the above arrangement, the micro-reaction chamber 110 can be heated by the portion of the heating electrode 12 that has a uniform working temperature to avoid being heated by the edge of the electrode 12 (for example, 5 mm, 8 mm from the edge, or other areas having a suitable size), so that the plurality of micro-reaction chambers 110 are heated more uniformly and their temperatures are more consistent, which is conducive to the effective amplification reaction of the reaction system solution in the micro-reaction chamber 110.

In the embodiment of the present disclosure, by providing the heating electrode 12 in the detection chip 100 (for example, integrating the heating electrode 12 on the first substrate 10), the micro-reaction chamber 110 of the detection chip 100 can be effectively heated, and then the temperature of the micro-reaction chamber 110 can be controlled without an external heating equipment, and thus the degree of integration is high. In addition, compared with some detection chips that need to drive liquid droplets to move through numerous temperature regions in sequence, the detection chip 100 can achieve the temperature cyclic process without driving liquid droplets, which is simple in operation and low in production costs.

For example, as shown in FIG. 3, the detection chip 100 further includes a hydrophilic layer 14 having the characteristics of hydrophilicity and oleophobicity. For example, the hydrophilic layer 14 covers the sidewall 1101 and the bottom 1102 of each of the plurality of micro-reaction chambers 110. Because the surface of the micro-reaction chamber 110 (i.e., the sidewall 1101 and the bottom 1102) is provided with the hydrophilic layer 14, the hydrophilicity of the micro-reaction chamber 110 is improved. In a case where no external driving force is applied to the reaction system solution, the reaction system solution may automatically and gradually enter each micro-reaction chamber 110 according to a capillary phenomenon, thereby realizing automatic sample input.

For example, as shown in FIG. 3, the hydrophilic layer 14 may also cover the surface of the micro-cavity defining layer 11 away from the first substrate 10, that is, the hydrophilic layer 14 is also provided on a spacing portion between the micro-reaction chambers 110. In this way, the hydrophilic layer 14 can completely cover the micro-cavity defining layer 11, so that the reaction system solution can more easily enter each micro-reaction chamber 110 to increase the sample input speed.

For example, the material of the hydrophilic layer 14 is a silicon oxide, such as silicon dioxide ($SiO_2$). Certainly, the embodiments of the present disclosure are not limited thereto, and the hydrophilic layer 14 may also be made of other suitable inorganic or organic materials, as long as the surface of the hydrophilic layer 14 away from the micro-cavity defining layer 11 is hydrophilic. For example, the hydrophilic layer 14 can be directly made of a hydrophilic material. For another example, the hydrophilic layer 14 may be made of a material having no hydrophilicity. In this case, it is necessary to hydrophilize the surface of the hydrophilic layer 14 away from the micro-cavity defining layer 11, so that the surface of the hydrophilic layer 14 away from the micro-cavity defining layer 11 is hydrophilic. For example, if a non-hydrophilic material such as silicon nitride is used, it can be hydrophilized, for example, by selecting methods such as a gelation modification method, an ultraviolet radiation method, a plasma method, etc. For example, a hydrophilic group can be formed on the surface of a non-hydrophilic material to make it hydrophilic.

For example, as shown in FIG. 3, the detection chip 100 further includes a second substrate 20 and a hydrophobic layer 13. The second substrate 20 is disposed opposite to the first substrate 10 and plays a role of protection, support, isolation, and the like. The hydrophobic layer 13 has the characteristics of hydrophobicity and lipophilicity, and is located on a side of the second substrate 20 facing the first substrate 10. The micro-cavity defining layer 11 is located on a side of the first substrate 10 facing the second substrate 20, and a surface of the micro-cavity defining layer 11 away from the first substrate 10 faces the second substrate 20. By providing the hydrophobic layer 13, the reaction system solution can enter each micro-reaction chamber 110 more easily.

For example, both the first substrate 10 and the second substrate 20 are glass substrates. The detection chip 100 is prepared by a micro-processing method adopting a glass substrate and in combination with semiconductor technology, which can realize large-scale mass production and can greatly reduce the corresponding production costs. It should be noted that, in various embodiments of the present disclosure, the first substrate 10 and the second substrate 20 may also be other suitable substrates, which is not limited in the embodiments of the present disclosure. For example, both the shape of the first substrate 10 and the shape of the second substrate 20 are rectangular. For example, in some examples, the size of the first substrate 10 is 3.2 cm*4.5 cm, and the size of the second substrate 20 is 3.2 cm*3 cm.

For example, the material of the hydrophobic layer 13 is a resin or a silicon nitride, for example, a commercial epoxy resin of DL-1001C. The hydrophobic layer 13 may also be made of other suitable inorganic or organic materials, as long as the side of the hydrophobic layer 13 facing the first substrate 10 is hydrophobic. For example, the hydrophobic layer 13 can be directly made of a hydrophobic material. For another example, the hydrophobic layer 13 may be made of a material having no hydrophobicity. In this case, it is necessary to hydrophobicize the surface of the hydrophobic layer 13 facing the first substrate 10, so that the surface of the hydrophobic layer 13 facing the first substrate 10 is hydrophobic.

In the embodiment of the present disclosure, the hydrophilic layer 14 and the hydrophobic layer 13 can jointly adjust the surface contact angle of the droplets of the reaction system solution, so that the detection chip 100 can realize self-priming liquid sample input and oil sealing. For example, in the detection chip 100, the hydrophobic performance outside the micro-reaction chamber 110 is improved by the hydrophobic layer 13, which makes the outside of the micro-reaction chamber 110 (for example, the surface of the second substrate 20 facing the micro-reaction chamber 110) hydrophobic, while the internal surface of the micro-reaction chamber has good hydrophilicity, so that the reaction system solution infiltrates from the outside of the micro-reaction chamber 110 to the inside of the micro-reaction chamber 110. Therefore, the reaction system solution can more easily enter each micro-reaction chamber 110 under the joint action of the hydrophilic layer 14 and the hydrophobic layer 13.

For example, as shown in FIG. 3, the detection chip 100 further includes a control electrode 15 and a first insulating layer 16. The control electrode 15 is located on the first substrate 10, the first insulating layer 16 covers the control electrode 15, and the heating electrode 12 is located on the first insulating layer 16. For example, the first insulating layer 16 includes a via 160 penetrating the first insulating layer 16. The control electrode 15 is electrically connected to the heating electrode 12 through the via 160, and is configured to apply an electrical signal (for example, a voltage signal) to the heating electrode 12. After receiving the electric signal, the heating electrode 12 can generate heat under the action of the electric signal to heat the micro-reaction chamber 110. It should be noted that the first insulating layer 16 may also cover a part of the first substrate 10 that is not blocked by the control electrode 15.

For example, the via 160 exposes a part of the control electrode 15 so that the heating electrode 12 can be electrically connected to the control electrode 15 through the via 160. The via 160 may be of a cylinder shape, a circular truncated cone shape, or the like. For example, the control electrode 15 may be electrically connected to the heating electrode 12 through one or more vias 160. When the electrical connection is implemented through more than one via 160, the connection resistance can be effectively reduced to reduce energy loss. When the electrical connection is implemented through one via 160, the production process can be simplified.

For example, the number of the control electrodes 15 may be one or more than one, which is not limited in the embodiments of the present disclosure. When more than one control electrode 15 is used to apply electrical signals to the heating electrode 12, different parts of the heating electrode 12 can receive the electrical signals at the same time, so that the heating of the heating electrode 12 is more uniform. For example, when there are a plurality of control electrodes 15, the first insulating layer 16 may include a plurality of vias 160, and each via 160 exposes a part of the control electrode 15, the heating electrode 12 is electrically connected to the plurality of control electrodes 15 through the plurality of vias 160, respectively. For example, there is a one-to-one correspondence between the plurality of control electrodes 15 and the plurality of vias 160. For another example, the number of the plurality of vias 160 may be greater than the number of the plurality of control electrodes 15, and each control electrode 15 is electrically connected to the heating electrode 12 through one or more vias 160.

It should be noted that, in the example shown in FIG. 3, the heating electrode 12 is located on a different layer from the control electrode 15. In some other embodiments, the heating electrode 12 may also be located on the same layer as the control electrode 15. In this case, the first insulating layer 16 may be omitted from the detection chip 100, and the heating electrode 12 and the control electrode 15 are electrically connected in an overlapping manner.

For example, the resistance value of the heating electrode 12 is greater than the resistance value of the control electrode 15, so that under the action of the same electrical signal, the heating electrode 12 generates more heat to heat the micro-reaction chamber 110, and the control electrode 15 generates less heat to reduce energy loss. For example, the control electrode 15 may be made of a material having a lower resistivity, thereby reducing the energy loss on the control electrode 15. The control electrode 15 may be made of a metal material, such as copper, copper alloy, aluminum, or aluminum alloy, and may be a single metal layer or a composite metal layer, which is not limited in the embodiments of the present disclosure.

For example, in some embodiments of the present disclosure, the heating electrode 12 is made of indium tin oxide (ITO) or tin oxide, and the control electrode 15 is made of a metal material. Because it is not easy to be oxidized, ITO can prevent the portion of the heating electrode 12 that is exposed to the air from being oxidized, thereby avoiding problems such as unevenly heating or increased power consumption caused by the oxidation of the heating electrode 12. Because of being covered by the first insulating layer 16, the control electrode 15 is not easy to be oxidized even if the control electrode 15 is made of a metal material.

For example, in order to facilitate the control electrode 15 to be electrically connected to a separately provided device to receive an electrical signal (for example, a voltage signal), the control electrode 15 may further include a contact portion 151 (as shown in FIG. 2, for example, a Pad area) that is not covered by the first insulating layer 16. For example, the contact portion 151 has a square shape of a large size, so that the contact portion 151 can be conveniently connected with a probe or an electrode in the separately provided device. Since the contact portion 151 has a large contact area, the contact portion 151 can stably receive an electrical signal. In this way, the detection chip 100 can be a plug-and-play device, simple in operation, and convenient to use. For example, when the control electrode 15 is made of a metal material, the contact portion 151 may be electroplated, thermally sprayed, or vacuum-plated to form a metal protective layer on the surface of the contact portion 151 in order to prevent the contact portion 151 from being oxidized without affecting its conductive performance.

For example, as shown in FIG. 3, the detection chip 100 further includes a second insulating layer 17. The second insulating layer 17 is located between the heating electrode 12 and the micro-cavity defining layer 11, that is, the second insulating layer 17 is located on the side of the heating electrode 12 away from the first substrate 10, and the micro-cavity defining layer 11 is located on the side of the second insulating layer 17 away from the heating electrode 12. The second insulating layer 17 is used to protect the heating electrode 12, provide an insulation function, prevent liquid from eroding the heating electrode 12, slow down the aging of the heating electrode 12, and can provide a planarization effect.

For example, the first insulating layer 16 and the second insulating layer 17 may be made of the same insulating material, such as an inorganic insulating material or an organic insulating material. For example, the first insulating layer 16 and the second insulating layer 17 are made of silicon dioxide, silicon nitride, or the like.

For example, as shown in FIGS. 2 and 3, the first substrate 10 includes a reaction region 101 and a peripheral region 102 at least partially surrounding the reaction region 101. For example, in some embodiments, in the second direction Y, the peripheral region 102 includes a first sub-region 102a and a second sub-region 102b located on opposite sides of the reaction region 101, respectively. For another example, in other embodiments, the peripheral region 102 completely surrounds the reaction region 101, that is, the peripheral region 102 is annular and surrounds the reaction region 101. For example, in this case, in the second direction Y, the peripheral region 102 includes a first sub-region 102a and a second sub-region 102b located on opposite sides of the reaction region 101, respectively, and in the first direction X, the peripheral region 102 further includes a third sub-region and a fourth sub-region located on opposite sides of the reaction region 101, respectively. The first sub-region 102a is connected with both the third and fourth sub-regions, and the second sub-region 102b is connected with both the third and fourth sub-regions, so that the peripheral region 102 surrounds the reaction region 101.

For example, in the example shown in FIG. 2, the size of the second substrate 20 is smaller than the size of the first substrate 10, and the second substrate 20 covers the reaction region 101. For example, the orthographic projection of the second substrate 20 on the first substrate 10 may completely overlap the reaction region 101. It should be noted that the embodiments of the present disclosure are not limited thereto. In some other examples, the size of the second substrate 20 may be the same as that of the first substrate 10. In this case, the second substrate 20 covers the reaction region 101 and the peripheral region 102, for example, the orthographic projection of the second substrate 20 on the first substrate 10 may completely overlap the first substrate 10.

For example, the control electrode 15 and the via 160 are located in the peripheral region 102, and the heating electrode 12 is located in the reaction region 101 and the peripheral region 102. For example, the reaction region 101 further includes a functional region 1010, and the micro-cavity defining layer 11 is located in the functional region 1010. For example, the orthographic projection of the heating electrode 12 on the first substrate 10 completely covers the functional region 1010 of the reaction region 101, that is, the functional region 1010 is located within the orthographic projection of the heating electrode 12 on the first substrate 10, thereby ensuring that the heating electrode 12 can heat each micro-reaction chamber 110.

For example, if a voltage signal (for example, a high voltage signal) is applied to the heating electrode 12 through only one control electrode 15 and a ground voltage is applied to the heating electrode 12 through another control electrode 15, a current path, for example, in the second direction Y, is formed for the heating electrode 12 so that the heating electrode 12 generates heat. Because the heating electrode 12 itself has a large resistance value, a large voltage drop is generated in a direction extending from the connection point between the heating electrode 12 and the control electrode 15 in the first direction X, so that the heating electrode 12 can be divided into a first partial electrode and a second partial electrode distributed in the first direction X. The first partial electrode receives a larger voltage signal, and the first partial electrode is, for example, an electrode portion at the connection point between the heating electrode 12 and the control electrode 15, and the second partial electrode receives a smaller voltage signal, and the second partial electrode is, for example, an electrode portion away from the connection point in the first direction X. Accordingly, the current in the heating electrode 12 is not uniform. The current in the first partial electrode is larger and the heat generated is larger, and the current in the second partial electrode is smaller and the heat generated is less. Therefore, when the heating electrode 12 is used for heating, the temperatures at different positions of the functional region 1010 may be different, so that the temperatures reached by the micro-reaction chambers 110 at different positions are different, which ultimately affects the amplification reaction of the reaction system solution in the micro-reaction chamber 110 and the accuracy of the detection results.

In view of the above problem, as shown in FIG. 2, a plurality of control electrodes 15 may be provided in the detection chip 100, and the plurality of control electrodes 15 may simultaneously transmit the same electrical signal to the heating electrode 12. For example, the plurality of control electrodes 15 may be uniformly distributed in the peripheral region 102, and the plurality of control electrodes 15 may simultaneously apply electrical signals to the heating electrodes 12 from different positions, so that the temperature uniformity at different positions in the functional region 1010 is improved, and the heat generated in different parts of the heating electrode 12 is approximately the same, therefore the temperature at different positions in the functional region 1010 is substantially the same. As shown in FIG. 2, in some examples, the detection chip 100 may include ten control electrodes 15, five of which are located in the first sub-region 102a of the peripheral region 102 and are uniformly arranged in the first direction X, and the other five of which are located in the second sub-region 102b of the peripheral region 102 and are uniformly arranged in the first direction X. The five control electrodes 15 in the first sub-region 102a or the second sub-region 102b apply voltage signals (for example, high-voltage signals) to the heating electrode 12, and the five control electrodes 15 in the second sub-region 102b or the first sub-region 102a apply, for example, a ground voltage to the heating electrode 12 to form a current path for the heating electrode 12, which can improve the uniformity of the current in the heating electrode 12, and further improve the temperature uniformity.

It should be noted that when, in the first direction X, the peripheral region 102 further includes a third sub-region and a fourth sub-region located on opposite sides of the reaction region 101, respectively, a plurality of control electrodes 15 may be provided in the third sub-region and the fourth sub-region. The number of control electrodes 15 and the positions of the control electrodes 15 are not limited in the embodiments of the present disclosure.

For example, as shown in FIG. 3, the detection chip 100 further includes a plurality of spacers 18. The plurality of spacers 18 are disposed in the peripheral region 102 and are located between the first substrate 10 and the second substrate 20. The plurality of spacers 18 are configured to maintain a distance between the first substrate 10 and the second substrate 20 so as to provide a space for the reaction system solution to flow. For example, in some embodiments, some spacers 18 may also be disposed in the reaction region 101, for example, separately disposed at numerous places in the reaction region 101, thereby improving the compressive strength of the detection chip 100 and preventing the reaction region 101 from being damaged by an external force. For example, the sizes and shapes of the plurality of spacers 18 may be the same as each other, thereby improving the thickness uniformity of the detection chip 100. For another example, the size and shape of the plurality of spacers 18 can also be set according to the pressure conditions that the detection chip 100 may be subjected to. For example, the size of the spacers 18 at the edge and center of the detection chip 100 is larger, while the size of the spacer 18 at the other positions is smaller.

For example, in a direction perpendicular to the first substrate 10, the height of the spacer 18 is greater than the height of the micro-cavity defining layer 11, and the first substrate 10, the micro-cavity defining layer 11, and the sealant including the spacer 18 jointly define the sample input channel and the sample output channel of the droplets of the reaction system solution, thereby ensuring that the droplets can move to each micro-reaction chamber 110 and the droplets that have not entered the micro-reaction chamber 110 flow out of the space between the first substrate 10 and the second substrate 20. For example, in some embodiments, the height of the spacer 18 is 30% or 50% greater than the height of the micro-cavity defining layer 11, and the specific proportional relationship between the height of the spacer 18 and the height of the micro-cavity defining layer 11 may be determined, for example, according to actual requirements, which is not limited in the embodiments of the present disclosure.

For example, the material of the spacer 18 may be a curable organic material, for example, a heat-curable material or a light-curable material, such as an ultraviolet (UV)-curable acrylic resin or other suitable materials. The shape of the spacer 18 may be spherical. In this case, the spacer 18 may be uniformly mixed in a sealant, and then the first substrate 10 and the second substrate 20 are cured and sealed by the sealant to make the first base plate 10 and the second base plate 20 to be aligned to form a cell. In this way, the spacer 18 mixed in the sealant can control the distance between the first substrate 10 and the second substrate 20. The embodiments of the present disclosure include, but are not limited thereto, the shape of the spacer 18 may also be any suitable shape such as a column, an ellipsoid, and the like.

For example, in some embodiments, as shown in FIG. 3, the detection chip 100 further includes a first temperature sensor 30. The first temperature sensor 30 is disposed on a side of the first substrate 10 away from the second substrate 20 (i.e., a side of the first substrate 10 away from the micro-cavity defining layer 11), and is located in the reaction region 101. The first temperature sensor 30 is configured to detect the temperature of the reaction region 101. For example, the temperature at the reaction region 101 is required to be maintained at a predetermined temperature (for example, 95° C., 55° C., or 72° C., etc.). In this case, the first temperature sensor 30 can detect the temperature at the reaction region 101 in real time, and then adjust the temperature at the reaction region 101 in real time through the heating electrode 12 to keep the temperature of the reaction region 101 at a predetermined temperature, thereby preventing the temperature of the reaction region 101 from being too high or too low to affect the amplification reaction. For example, the first temperature sensor 30 may be various types of temperature sensors, such as a contact temperature sensor or a non-contact temperature sensor, for example, a thermocouple temperature sensor or an infrared temperature sensor.

For example, as shown in FIGS. 2 and 3, the detection chip 100 further includes at least one sample inlet 21 and at least one sample outlet 22. Both the sample inlet 21 and the sample outlet 22 penetrate the second substrate 20 and the hydrophobic layer 13. For example, the reaction system solution can be injected into the sample inlet 21 through a micro-injection pump or a pipetting gun, and then entered into each micro-reaction chamber 110 through self-priming.

For example, the reaction region 101 also includes a non-functional region 1011. Both the sample inlet 21 and the sample outlet 22 are located in the non-functional region 1011 and on different sides of the functional region 1010. For example, as shown in FIG. 2, in the second direction Y, the sample inlet 21 and the sample outlet 22 are located on opposite sides of the functional region 1010, respectively. For example, the sample inlet 21 and the sample outlet 22 are symmetrically distributed with respect to the first direction X, so that the flow of the reaction system solution in the detection chip 100 can be more uniform, thereby facilitating the reaction system solution to enter each micro-reaction chamber 110. Certainly, the embodiments of the present disclosure are not limited thereto, and the sample inlets 21 and the sample outlet 22 may also be symmetrically distributed with respect to the second direction Y or any other arbitrary direction. It should be noted that both the sample inlet 21 and the sample outlet 22 may also be located in the functional region 1010.

Figure 4A:
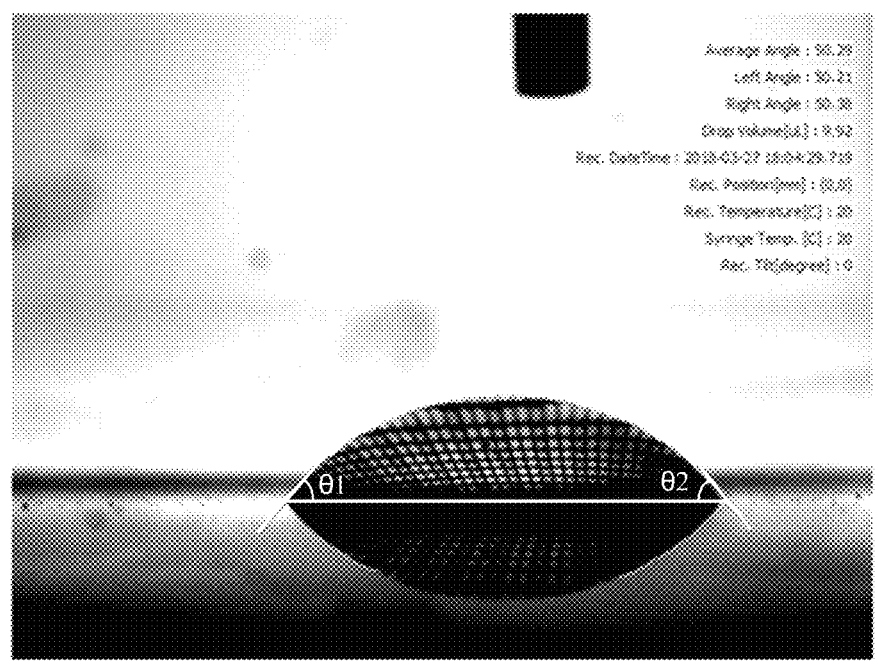
FIG. 4A is a schematic diagram of performing a hydrophilicity and hydrophobicity test on a surface of a micro-reaction chamber before surface modification provided by some embodiments of the present disclosure.
Figure 4B:
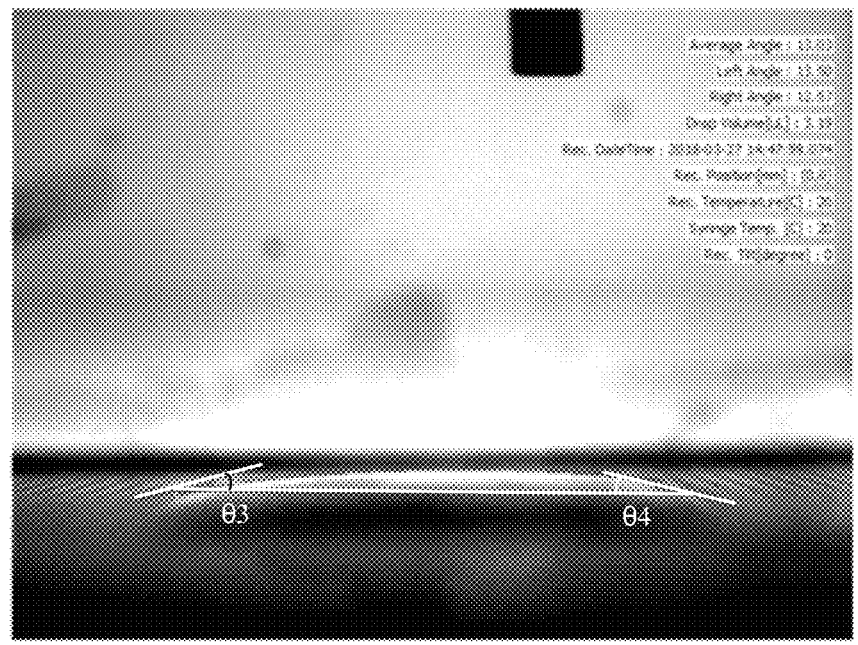
FIG. 4B is a schematic diagram of performing a hydrophilicity and hydrophobicity test on a surface of a micro-reaction chamber after surface modification provided by some embodiments of the present disclosure.

FIG. 4A is a schematic diagram of performing a hydrophilicity and hydrophobicity test on a surface of a micro-reaction chamber before surface modification provided by some embodiments of the present disclosure, and FIG. 4B is a schematic diagram of performing a hydrophilicity and hydrophobicity test on a surface of a micro-reaction chamber after surface modification provided by some embodiments of the present disclosure. Here, the "micro-reaction chamber before surface modification" refers to a micro-reaction chamber without a hydrophilic layer provided on the bottom and sidewalls of the micro-reaction chamber, and is hereinafter referred to as a first micro-reaction chamber; and the "micro-reaction chamber after surface modification" refers to a micro-reaction chamber with a hydrophilic layer provided on the bottom and sidewalls of the micro-reaction chamber, i.e., the micro-reaction chamber 110 in the detection chip 100 provided in the embodiment of the present disclosure, and is hereinafter referred to as a second micro-reaction chamber.

For example, in the testing process shown in FIG. 4A and FIG. 4B, a deionized water droplet is used as a test droplet, and a contact angle of the droplet on the surface (the bottom or sidewalls) of the micro-reaction chamber is tested. As shown in FIG. 4A, a volume of a first test droplet is 9.92 µL. For the first micro-reaction chamber, a left contact angle $\theta 1$ between the first test droplet and the surface of the first micro-reaction chamber is about 50.38°, a right contact angle $\theta 2$ between the first test droplet and the surface of the first micro-reaction chamber is about 50.21°, and thus an average contact angle between the first test droplet and the surface of the first micro-reaction chamber is about 50.29°. As shown in FIG. 4B, a volume of a second test droplet is 3.19 µL. For the second micro-reaction chamber, a left contact angle $\theta 3$ between the second test droplet and the surface of the second micro-reaction chamber is about 12.57°, a right contact angle $\theta 4$ between the second test droplet and the surface of the second micro-reaction chamber is about 13.50°, and thus an average contact angle between the second test droplet and the surface of the second micro-reaction chamber is about 13.03°. It can be seen that, in some embodiments of the present disclosure, the hydrophilic layer 14 is provided on the surface of the micro-reaction chamber 110, so the hydrophilicity is greatly improved, therefore the contact angle between the droplet and the surface of the micro-reaction chamber 110 is smaller.

Figure 5A:
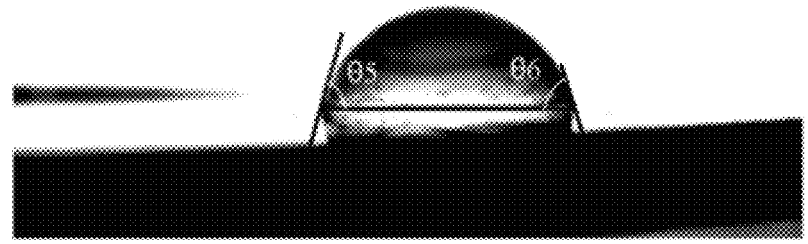
FIG. 5A is a schematic diagram of performing a hydrophilicity and hydrophobicity test on a surface of a second substrate of a detection chip provided by some embodiments of the present disclosure.
Figure 5B:
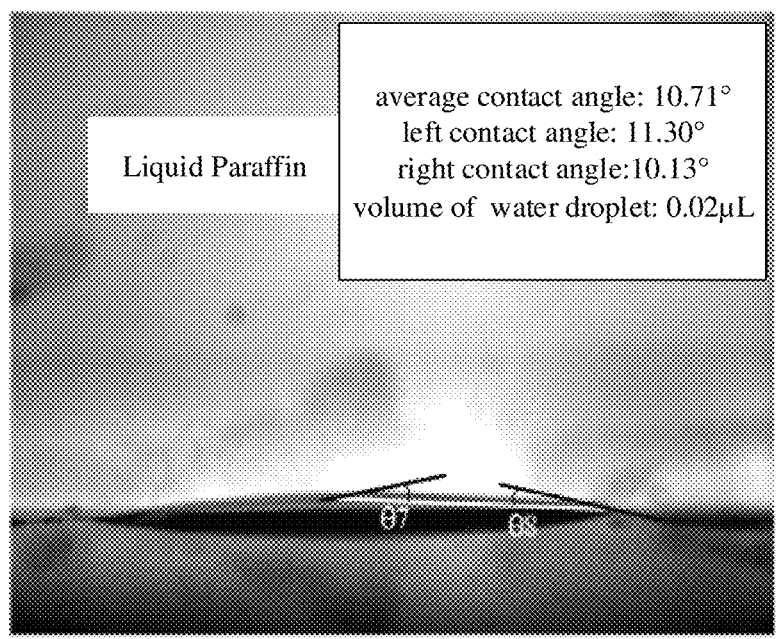
FIG. 5B is a schematic diagram of performing a hydrophilicity and hydrophobicity test on a surface of a second substrate of a detection chip provided by some other embodiments of the present disclosure.

FIG. 5A is a schematic diagram of performing a hydrophilicity and hydrophobicity test on a surface of a second substrate of a detection chip provided by some embodiments of the present disclosure, and FIG. 5B is schematic diagram of performing a hydrophilicity and hydrophobicity test on a surface of a second substrate of a detection chip provided by other embodiments of the present disclosure.

For example, in the testing process shown in FIG. 5A, a deionized water droplet is used, and a contact angle of the droplet on the surface of the hydrophobic layer 13 on the second substrate 20 is tested. For example, the volume of the water droplet is 4.45 µL, a left contact angle $\theta 5$ between the water droplet and the surface of the hydrophobic layer 13 on the second substrate 20 is about 73.83°, a right contact angle $\theta 6$ between the water droplet and the surface of the hydrophobic layer 13 on the second substrate 20 is about 74.0°, and thus an average contact angle between the water droplet and the surface of the hydrophobic layer 13 on the second substrate 20 is about 72.92°. In the testing process shown in FIG. 5B, a liquid paraffin is used, and a contact angle of the liquid paraffin on the surface of the hydrophobic layer 13 on the second substrate 20 is tested. For example, the volume of the liquid paraffin is 0.02 µL, a left contact angle $\theta 7$ between the liquid paraffin and the surface of the hydrophobic layer 13 on the second substrate 20 is about 10.13°, a right contact angle $\theta 8$ between the liquid paraffin and the surface of the hydrophobic layer 13 on the second substrate 20 is about 11.30°, and thus an average contact angle between the liquid paraffin and the surface of the hydrophobic layer 13 on the second substrate 20 is about 10.71°. It can be seen that, in some embodiments of the present disclosure, the hydrophobic layer 13 is provided on the surface of the second substrate 20, so that the hydrophobicity is greatly improved, therefore the contact angle between the water droplet and the surface of the hydrophobic layer 13 on the second substrate 20 is large, while the contact angle between the liquid paraffin and the surface of the hydrophobic layer 13 on the second substrate 20 is small.

Figure 6A:
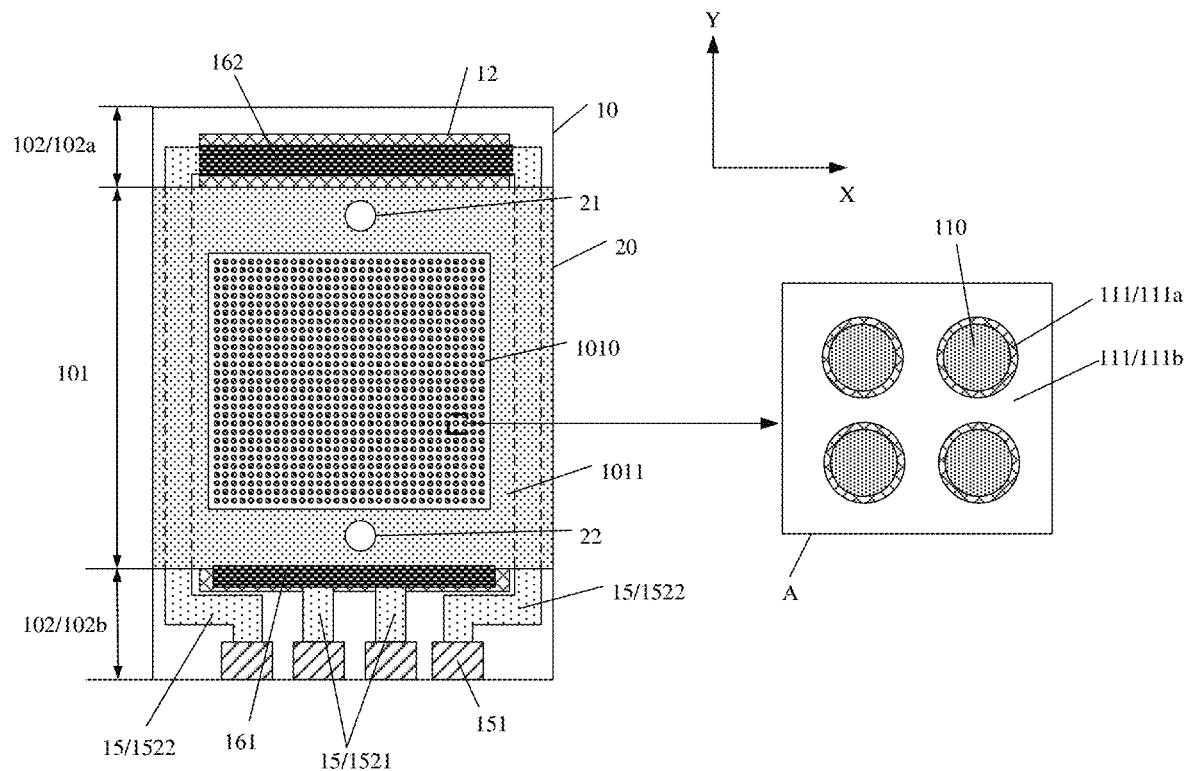
FIG. 6A is a schematic plane view of another detection chip provided by some embodiments of the present disclosure.
Figure 6B:
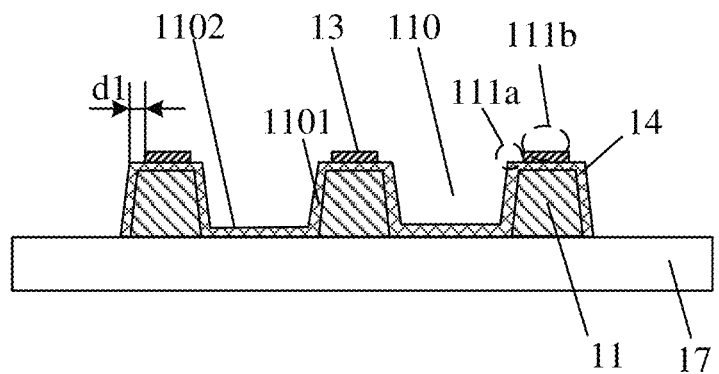
FIG. 6B is a schematic structural diagram of a partial cross-section of another detection chip provided by some embodiments of the present disclosure.

FIG. 6A is a schematic plane view of another detection chip provided by some embodiments of the present disclosure, and FIG. 6B is a schematic structural diagram of a partial cross section of another detection chip provided by some embodiments of the present disclosure. For example, as shown in FIGS. 6A and 6B, except the different arrangement of the hydrophilic layer 14 and the hydrophobic layer 13 and the different arrangement of the control electrode 15, the detection chip 100 of this embodiment is substantially the same as the detection chip 100 shown in FIGS. 2 and 3. The following describes the arrangement of the hydrophilic layer 14 and the hydrophobic layer 13 and the arrangement of the control electrode 15 in the detection chip 100 provided in this embodiment. For other structures, reference may be made to the related descriptions in FIG. 2 and FIG. 3, and details are not described herein again.

For example, as shown in FIGS. 6A and 6B, each of the plurality of micro-reaction chambers 110 includes a reaction well including a sidewall 1101 and a bottom 1102. The micro-cavity defining layer 11 includes a spacing region 111 located between the micro-reaction chambers 110. The spacing region 111 includes a first region 111a adjacent to the sidewall 1101 of the plurality of micro-reaction chambers 110 and a second region 111b not adjacent to the sidewall 1101 of the plurality of micro-reaction chambers 110. The hydrophilic layer 14 covers the sidewall 1101 and the bottom 1102 of each of the plurality of micro-reaction chambers 110, and also covers the first region 111a of the spacing region 111 of the micro-cavity defining layer 11. The hydrophobic layer 13 covers the second region 111b of the spacing region 111 of the micro-cavity defining layer 11.

In this way, the portion of the spacing region 111 of the micro-cavity defining layer 11 that is next to the micro-reaction chamber 110 can be hydrophilic, that is, the upper edge of the sidewall 1101 can be hydrophilic, so that the self-priming effect of the reaction system solution can be better achieved, therefore the droplets of the reaction system solution can more easily enter the respective micro-reaction chamber 110 (i.e., the reaction well) to avoid liquid interference.

For example, the first region 111a is a circular ring having a width d1 of 2 µm to 5 µm, for example, 3 µm. Certainly, the embodiments of the present disclosure are not limited thereto, and the first region 111a may also be other shapes, for example, depending on the cross-sectional shape of the micro-reaction chamber 110. For example, the first region 111a may be a rectangular ring when the cross-sectional shape of the micro-reaction chamber 110 is rectangular, and the first region 111a may be an oval ring when the cross-sectional shape of the micro-reaction chamber 110 is oval. The width d1 of the first region 111a is also not limited, and can be determined according to the self-priming effect actually required and the processing technology.

For example, the hydrophilic layer 14 may be formed on the micro-cavity defining layer 11 first. The hydrophilic layer 14 covers the sidewall 1101 and the bottom 1102 of the micro-reaction chamber 110, and covers the spacing region 111 of the micro-cavity defining layer 11. The hydrophobic layer 13 is then formed on the second region 111b, thereby realizing the structure shown in FIGS. 6A and 6B. For example, in the second region 111b, the hydrophilic layer 14 and the hydrophobic layer 13 laminate on the micro-cavity defining layer 11, and the hydrophobic layer 13 may be in contact with the reaction system solution. In this way, the above structure can be realized while simplifying the production process (for example, simplifying the deposition process of the hydrophilic layer 14 without patterning the hydrophilic layer 14), thereby reducing production costs. Certainly, the embodiments of the present disclosure are not limited thereto. In other embodiments, in the second region 111b, the micro-cavity defining layer 11 may be covered only with the hydrophobic layer 13 instead of forming a stacked structure of the hydrophilic layer 14 and the hydrophobic layer 13 thereon, which may be determined according to the actual processing technology and production method.

Figure 6C:
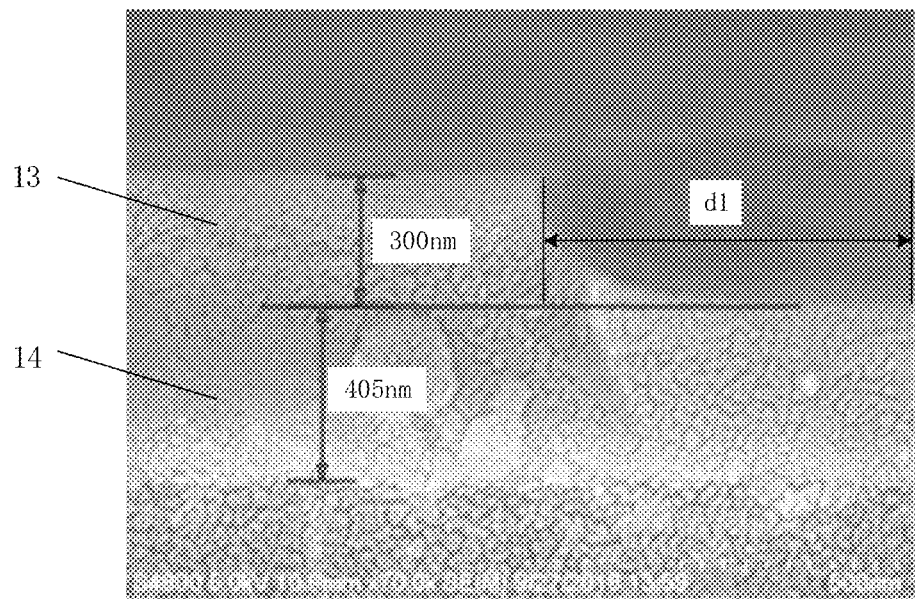
FIG. 6C is a schematic scanning electron microscope photograph of a micro-cavity defining layer, a hydrophilic layer, and a hydrophobic layer of another detection chip provided by some embodiments of the present disclosure.

FIG. 6C is a schematic scanning electron microscope photograph of a micro-cavity defining layer, a hydrophilic layer, and a hydrophobic layer of another detection chip according to some embodiments of the present disclosure. For example, as shown in FIG. 6C, the thickness of the hydrophilic layer 14 is 405 nm, the thickness of the hydrophobic layer 13 is 300 nm, and the width d1 of the first region 111a is greater than 300 nm.

For example, as shown in FIG. 6A, the vias 160 in the first insulating layer 16 include a first via group 161 and a second via group 162, and each via group includes one or more through holes penetrating the first insulating layer 16. The first via group 161 and the second via group 162 are located on opposite sides of the peripheral region 102, respectively. For example, the first via group 161 is located in the second sub-region 102b, and the second via group 162 is located in the first sub-region 102a. The control electrode 15 includes a first control electrode group 1521 and a second control electrode group 1522. The first control electrode group 1521 is located on the same side as the first via group 161 in the peripheral region 102, that is, in the second sub-region 102b. The first control electrode group 1521 is electrically connected to the heating electrode 12 through the first via group 161. The second control electrode group 1522 extends along the peripheral region 102 and partially surrounds the heating electrode 12. For example, the second control electrode group 1522 extends from the second sub-region 102b into the first sub-region 102a along the edge of the heating electrode 12, and is electrically connected to the heating electrode 12 through the second via group 162. For example, the control electrode 15 includes a contact portion 151. The contact portion 151 has a square shape of a large size, so that the contact portion 151 can be conveniently connected with a probe or an electrode in a separately provided device, and since the contact area of the contact portion 151 is large, the electrical signal can be stably received.

In this way, the control electrode 15 can at least partially surround the heating electrode 12, which can reduce the heat loss of the heating electrode 12, make the temperature of the reaction region 101 more uniform, and improve the heating efficiency of the heating electrode 12, thereby reducing power consumption.

At least one embodiment of the present disclosure further provides a reaction system including a control device and a detection chip according to any one of the embodiments of the present disclosure. The reaction system can effectively control the temperature of the micro-reaction chamber of the detection chip, and the temperature cyclic process can be realized without driving droplets and without external heating equipment. Therefore, the reaction system has a high degree of integration, is simple in operation and low in production costs, and can achieve effective sample input.

Figure 7:
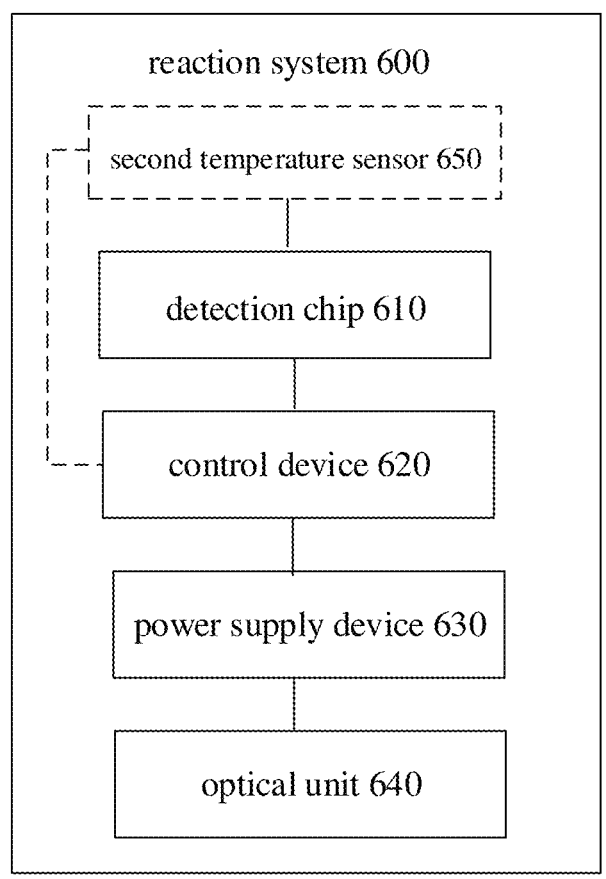
FIG. 7 is a schematic block diagram of a reaction system provided by some embodiments of the present disclosure.

FIG. 7 is a schematic block diagram of a reaction system provided by some embodiments of the present disclosure. For example, as shown in FIG. 7, a reaction system 600 includes a detection chip 610, a control device 620, and a power supply device 630 that provides a signal voltage, a driving voltage, and the like to the detection chip 610 and the control device 620. The detection chip 610 is the detection chip according to any embodiment of the present disclosure, such as the aforementioned detection chip 100. The control device 620 is electrically connected to the detection chip 610, and is configured to apply an electrical signal to the detection chip 610 to drive the heating electrode of the detection chip 610. For example, the plurality of micro-reaction chambers of the detection chip 610 may accommodate the reaction system solution. The control device 620 applies an electric signal to the heating electrode of the detection chip 610 to cause the heating electrode to release heat, so as to control the temperature of the functional region of the detection chip 610 to perform an amplification reaction on the reaction system solution. For example, the control device 620 may be implemented as general-purpose or special-purpose hardware, software, or firmware, and the like, and may further include, for example, a central processing unit (CPU), an embedded processor, a programmable logic controller (PLC), and the like, which is not limited in the embodiments of the present disclosure.

For example, the reaction system 600 may further include a second temperature sensor 650. For example, when the detection chip 610 is substantially the same as the detection chip 100 shown in FIG. 3 but does not include the first temperature sensor 30, the second temperature sensor 650 is required to be provided in the reaction system 600, and the second temperature sensor 650 is required to be provided at a position substantially the same as the first temperature sensor 30 in the detection chip 100, so as to realize a function of detecting temperature. For example, the second temperature sensor 650 is disposed on a side of the first substrate of the detection chip 610 away from the microcavity defining layer, and is located in the reaction region of the first substrate. The second temperature sensor 650 is configured to detect a temperature of the reaction region of the detection chip 610. For example, the second temperature sensor 650 may be any types of temperature sensors, for example, a contact temperature sensor or a non-contact temperature sensor, such as a thermocouple temperature sensor or an infrared temperature sensor. It should be noted that, in some other embodiments, in the case where the detection chip 610 is the detection chip 100 shown in FIG. 3, the detection chip 100 includes the first temperature sensor 30, so there is no need to provide a second temperature sensor 650 in the reaction system 600.

For example, the reaction system 600 may further include an optical unit 640 configured to perform optical detection on the detection chip 610. For example, the optical unit 640 includes a fluorescence detection device configured to perform fluorescence detection on a solution to be detected in a plurality of micro-reaction chambers. For example, the fluorescence detection device may include a fluorescent light source and an image sensor (e.g., a charge-coupled device (CCD) image sensor). It should be noted that the "solution to be detected" is a solution obtained by performing the polymerase chain reaction on the reaction system solution, i.e., the reaction system solution after the amplification reaction is completed. For example, the optical unit 640 may further include an image processing device configured to process a detection picture output by the fluorescence detection device. For example, the image processing device may include a central processing unit (CPU) or a graphics processing unit (GPU), and the like. For example, the control device 620 is also configured to control the fluorescence detection device and the image processing device to perform corresponding functions.

The working principle and process of the reaction system 600 are described as follows.

First, the reaction system solution is prepared. For example, the reaction system solution may include a cell lysate, a PCR amplification reagent and a DNA fragment sample solution after being cleaved by a DNA lyase. For example, in an example, the DNA to be detected is exon 19 of the epidermal growth factor receptor (EGFR) gene, and accordingly, the PCR amplification reagent contains a specific PCR amplification primer for exon 19 of the EGFR gene. For example, the volume of the reaction system solution is 20 microliters, and the reaction system solution includes 10 microliters of a MIX reagent (the MIX reagent includes Taq enzymes, dNPTs, and $MgCl_2$), 0.6 microliters of an upstream primer (10 mmol (mM)), 0.6 microliters of a downstream primer (10 mM), 7.8 microliters of water, and 1 microliter of fully diluted template DNA to ensure that the number of template DNA in each micro-reaction chamber is less than or equal to 1.

Then, a polytetrafluoroethylene connector and a silica gel tube are installed in the sample inlet of the detection chip 610, and the prepared reaction system solution is injected into the sample inlet through a micro-injection pump or a pipetting gun. The reaction system solution enters the sample inlet through the polytetrafluoroethylene connector and the silica gel tube, and then enters each microreaction chamber by self-priming under the cooperation of the hydrophilic layer and the hydrophobic layer.

Figure 8A:
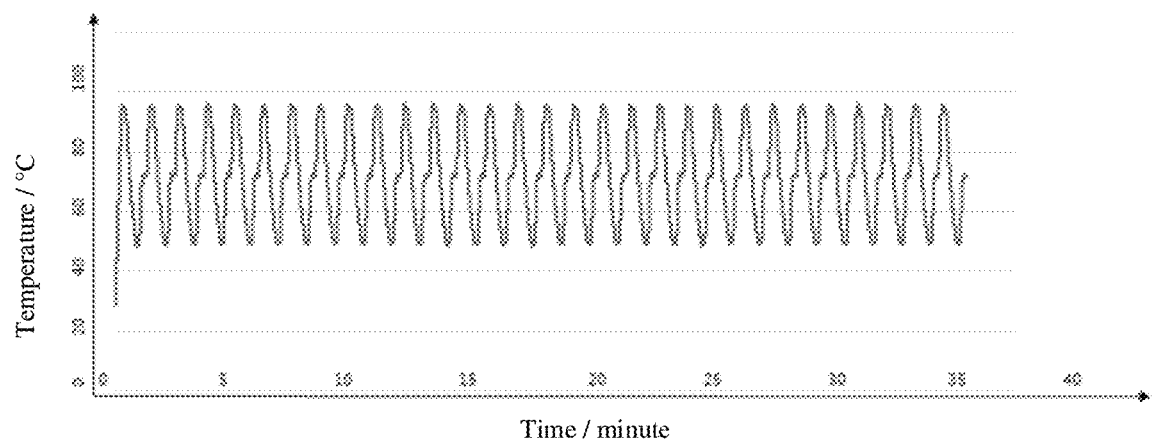
FIG. 8A is a relationship curve between temperature and time when a reaction system performs a thermal cycling process according to some embodiments of the present disclosure.
Figure 8B:
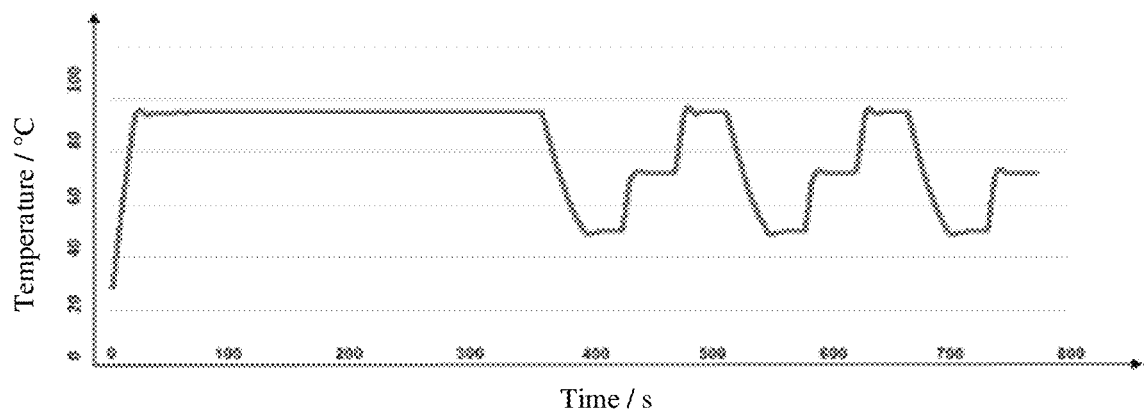
FIG. 8B is a relationship curve between temperature and time including a pre-denaturation process when a reaction system performs a thermal cycling process provided by some embodiments of the present disclosure.

Next, a three-step method is used to perform the thermal cycling amplification on dPCR. The oil-sealed detection chip 610 is placed on a chip carrier of the reaction system 600 and fixed by a fixture, and the electrode is electrically connected to the control electrode of the detection chip 610. The parameters are set by, for example, a parameter setting button. The cycle parameters are denaturation at 95° C. for 15 seconds, annealing at 55° C. for 45 seconds, and extension at 72° C. for 45 seconds. A total of 30 thermal cycles are set. For example, pre-denaturation at 95° C. for 5 minutes can also be set. The droplets in the micro-reaction chamber containing the template DNA in the detection chip 610 are subjected to the PCR amplification reaction, while the droplets in the micro-reaction chamber without the template DNA are used as the comparison group. For example, the relationship curves between the temperature and time of the thermal cycle are shown in FIGS. 8A and 8B. It can be seen that the temperature control effect of the thermal cycle is good and accurate temperature control can be achieved.

Figure 8C:
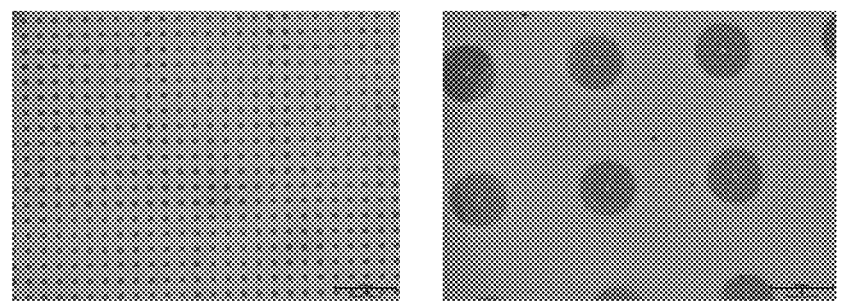
FIG. 8C is an effect diagram of a detection chip of a reaction system after self-priming liquid sample loading and oil sealing provided by some embodiments of the present disclosure.

It should be noted that, before performing PCR amplification, the micro-reaction chamber can be filled with 0.2 wt % bovine serum albumin (BSA) solution and soaked for 1 hour to reduce the adsorption of PCR reagents and sample templates by the internal surface of the micro-reaction chamber in order to improve the reaction efficiency and detection accuracy. Then, the BSA solution was drawn by a micro-pump, and the reaction system solution is injected into the micro-reaction chamber, and then the micro-reaction chamber is sealed with an oil phase liquid. For example, the effect of self-priming liquid sample loading and oil sealing is shown in FIG. 8C. For example, sealing by an oil phase liquid can use mineral oil, liquid paraffin, isopropyl palmitate, butyl laurate, perfluoroalkane oil, etc., to seal the sample inlet and sample outlet to prevent the reaction system solution from volatilizing.

Figure 8D:
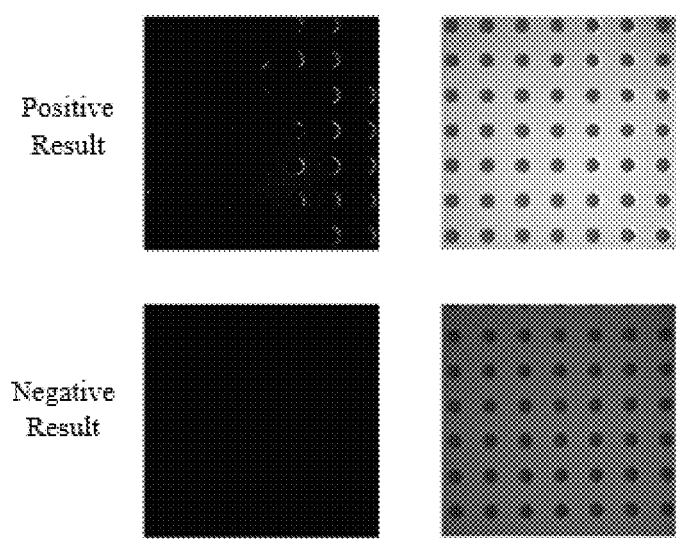
FIG. 8D is a comparison diagram of negative and positive results of a gene mutation in the epidermal growth factor receptor (EGFR) of exon 19 provided by some embodiments of the present disclosure.

After 30 cycles of amplification, the detection chip 610 is taken out and then observed by a fluorescence microscope with an excitation wavelength of 450 nm to 480 nm, thereby obtaining the positive and negative results comparison as shown in FIG. 8D. For example, as shown in FIG. 8D, when the reaction system solution contains an EGFR exon 19 with a genic mutation, because the reaction solution contains the specific PCR amplification primer for the EGFR exon 19 with the genic mutation, the exon 19 with the genic mutation was greatly amplified under the action of the PCR amplification primer, so that the solution to be tested shows a positive result, that is, a fluorescent reaction appeared in at least part of the micro-reaction chamber. When the reaction system solution does not contain an EGFR exon 19 with a genic mutation, the solution to be tested shows a negative result, that is, no fluorescence reaction occurs in all micro-reaction chambers. This enables detection of the EGFR exon 19.

At least one embodiment of the present disclosure also provides a using method of the detection chip, by which the detection chip according to any embodiment of the present disclosure can be operated. With this using method, the temperature of the micro-reaction chamber of the detection chip can be effectively controlled, the temperature cyclic process can be realized without driving the droplet and without the external heating equipment. Therefore, the degree of integration is high, the operation is simple, the production costs are low and effective sample input can be achieved.

Figure 9:
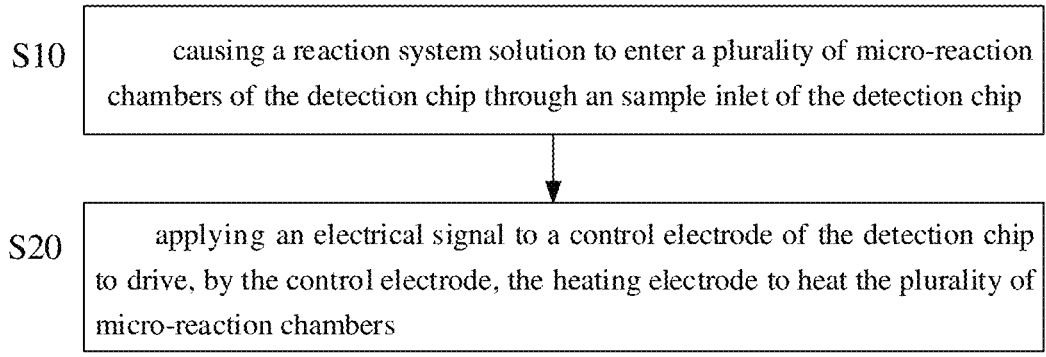
FIG. 9 is a schematic flowchart of a using method of a detection chip provided by some embodiments of the present disclosure.

FIG. 9 is a schematic flowchart of a using method of the detection chip according to some embodiments of the present disclosure. For example, as shown in FIG. 9, the using method includes the following operations:

Step S10: causing the reaction system solution to enter the plurality of micro-reaction chambers 110 of the detection chip 100 through the sample inlet 21 of the detection chip 100;

Step S20: applying an electrical signal to the control electrode 15 of the detection chip 100 to drive the heating electrode 12 by the control electrode 15 to heat the plurality of micro-reaction chambers 110.

For example, the using method further includes cooling the plurality of micro-reaction chambers 110 to change the temperature of the plurality of micro-reaction chambers 110, so that the reaction system solution in the plurality of micro-reaction chambers 110 undergoes a temperature cyclic process including a denaturation stage, an annealing stage, and an extension stage. For example, the micro-reaction chambers can be cooled by air cooling equipment, which is simple in structure and easy to implement.

For example, the using method further includes performing optical detection on the detection chip 100 to obtain a fluorescent image.

It should be noted that, in some embodiments of the present disclosure, the using method may further include more steps, which may be determined according to actual requirements, which is not limited in the embodiments of the present disclosure. For detailed descriptions and technical effects of the using method, reference may be made to the above descriptions of the detection chip 100 and the reaction system 600, and details are not described herein again.

The preparation method of the detection chip 100 provided by some embodiments of the present disclosure will be briefly described below.

The preparation method of the detection chip 100 includes the following operations: forming a heating electrode 12 on the first substrate 10; forming on the first substrate 10 a micro-cavity defining layer 11, which defines a plurality of micro-reaction chambers 110.

For example, forming the heating electrode 12 on the first substrate 10 may include: sputtering an electrically conductive layer (for example, an ITO layer) on a side of the first insulating layer 16 away from the first substrate 10, and then sequentially performing processes such as exposing, developing, dry etching, peeling, and the like on the conductive layer to obtain the heating electrode 12.

For example, the micro-reaction chamber 110 can be directly prepared on the first substrate 10 through a semiconductor patterning process (including a photolithography process and plasma vapor deposition, etc.), and the process is simple to enable large-scale mass production with low production costs.

For example, forming the micro-cavity defining layer 11 includes: depositing a defining material layer on the first substrate 10; and performing a patterning process on the defining material layer to obtain the micro-cavity defining layer 11. The defining material layer may be a photoresist layer. Performing the patterning process on the defining material layer to obtain the micro-cavity limiting layer 11 includes: exposing and developing the defining material layer using a mask to form a plurality of micro-reaction chambers 110 in the defining material layer in order to obtain the micro-cavity defining layer 11.

For example, the preparation method further includes: forming a hydrophilic layer 14 on a surface of the micro-cavity defining layer 11 away from the first substrate 10, and forming a hydrophilic layer 14 on a sidewall 1101 and a bottom 1102 of the plurality of micro-reaction chambers 110.

Figure 10A:
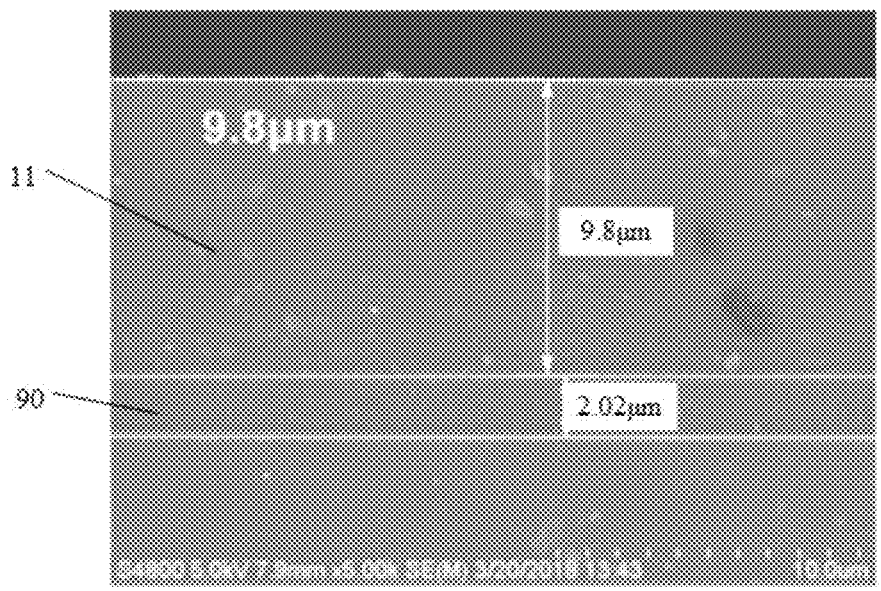
FIG. 10A is a schematic diagram of a scanning electron microscope of a micro-cavity defining layer of a detection chip provided by some embodiments of the present disclosure.
Figure 10B:
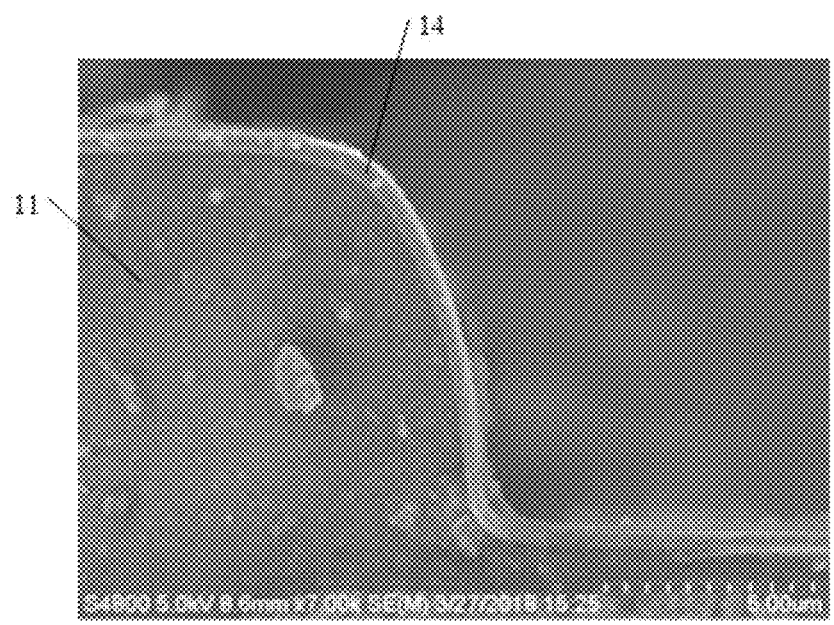
FIG. 10B is a schematic scanning electron microscope photograph of a micro-cavity defining layer and a hydrophilic layer of a detection chip provided by some embodiments of the present disclosure.

For example, in some embodiments, the process of forming the micro-cavity defining layer 11 is described as follows. First, the first substrate 10 is provided, and the optical adhesive 90 (i.e., OC adhesive) is spin-coated at a speed of 1500 revolutions per minute for 45 seconds, and then the optical adhesive is cured at 230° C. for 30 minutes. On the first substrate 10 after the optical adhesive 90 is coated, a photoresist (for example, the model is KMH-T546, and thermal weight loss temperature is 320° C.) is spin-coated at a speed of 300 revolutions per minute, and the photoresist was baked at 90° C. for 2 minutes. The photoresist is spin-coated again and the above process is performed to obtain a photoresist layer. Next, the photoresist layer is exposed through a mask to obtain a target pattern. The exposure intensity is 999 mJ, the gap value (i.e., the distance between the mask and the first substrate 10) is 100 microns, and the exposure time is 15 seconds. The exposed photoresist layer is developed with a developing solution for 45 seconds, and the developed photoresist layer is cured at a temperature of 230° C. for 30 minutes to finally obtain the micro-cavity defining layer 11. As shown in FIG. 10A, the thickness of the optical adhesive 90 is about 2.02 microns, and the thickness of the micro-cavity defining layer 11 is about 9.8 microns. As shown in FIG. 10B, after the micro-cavity defining layer 11 is obtained, a silicon dioxide layer can be deposited on the micro-cavity defining layer 11 by means of plasma enhanced chemical vapor deposition (PECVD) to obtain the hydrophilic layer 14. The thickness of the hydrophilic layer 14 is about 300 nm, and the hydrophilic layer 14 completely covers the surface of the micro-cavity defining layer 11.

It should be noted that, before these film layers are formed on the first substrate 10 and the second substrate 20, the first substrate 10 and the second substrate 20 may be cleaned so as to facilitate the deposition of a material layer on the first substrate 10 and the second substrate 20.

For example, forming the control electrode 15 on the first substrate 10 may include: sputtering a metal conductive layer on the first substrate 10, and then sequentially performing processes such as exposing, developing, etching, peeling, and the like on the metal conductive layer to obtain the control electrode 15. For example, the metal conductive layer is a stacked layer formed of molybdenum-aluminum-neodymium-molybdenum (Mo—AlNd—Mo).

For example, forming the first insulating layer 16 on the first substrate 10 includes: depositing through a deposition process an insulating material layer on the first substrate 10 on which the control electrode 15 is formed, and then performing processes such as exposing, developing, via etching, peeling, and the like on the insulating material layer to obtain the first insulating layer 16. For example, a via 160 may be formed in the first insulating layer 16.

For example, forming the second insulating layer 17 on the first substrate 10 includes: depositing an insulating layer (for example, a silicon dioxide layer and/or a silicon nitride layer) on a surface of the heating electrode 12 away from the first insulating layer 16 to obtain the second insulation layer 17.

It should be noted that, in the above-mentioned preparation method, a semiconductor preparation process may be adopted to prepare the heating electrode 12, the control electrode 15, the first insulating layer 16, the second insulating layer 17, and the like.

For example, forming the sample inlet 21 and the sample outlet 22 may include: firstly preparing a first through hole and a second through hole on the second substrate 20 through laser array drilling, and then forming a third through hole and a fourth through hole in the hydrophobic layer 13 through a patterning process. The first through hole exposes the third through hole, the second through hole exposes the fourth through hole, the first through hole and the third through hole constitute the sample inlet 21, and the second through hole and the fourth through hole constitute the sample outlet 22.

For example, the preparation method further includes: curing a sealant to seal the first substrate 10 and the second substrate 20. The sealant includes a plurality of spacers 18, and the plurality of spacers 18 may be spherical.

The following statements should be noted:
(1) The accompanying drawings involve only the structure(s) in connection with the embodiment(s) of the present disclosure, and other structure(s) can be referred to common design(s).
(2) In case of no conflict, features in one embodiment or in different embodiments can be combined.

What are described above is related to the illustrative embodiments of the present disclosure only and not limitative to the scope of the present disclosure; the scopes of the present disclosure are defined by the accompanying claims.

What is claimed is:

1. A detection chip, comprising:
    a first substrate;
    a micro-cavity defining layer, being on the first substrate and defining a plurality of micro-reaction chambers; and
    a heating electrode, located between the first substrate and the micro-cavity defining layer, and configured to heat the plurality of micro-reaction chambers,
    wherein an orthographic projection of the plurality of micro-reaction chambers on the first substrate is within an orthographic projection of the heating electrode on the first substrate;
    the plurality of micro-reaction chambers comprises a first micro-reaction chamber and a second micro-reaction chamber spaced apart from each other, and the heating electrode continuously extends from a first position corresponding to the first micro-reaction chamber to a second position corresponding to the second micro-reaction chamber;
    the heating electrode comprises one continuous electrode, orthographic projections of the plurality of micro-reaction chambers on the first substrate are within an orthographic projection of the one continuous electrode on the first substrate.

2. The detection chip of claim 1, wherein the heating electrode comprises:
    a first electrode part, located at the first position between the first substrate and the first micro-reaction chamber; and
    a second electrode part, located at the second position between the first substrate and the second micro-reaction chamber, and the first electrode part is connected to the second electrode part.

3. The detection chip of claim 2, wherein the heating electrode further comprises a third electrode part between the first electrode part and the second electrode part, and the first electrode part is connected to the second electrode part through the third electrode part.

4. The detection chip of claim 3, wherein the micro-cavity defining layer comprises a spacing region between the first micro-reaction chamber and the second micro-reaction chamber, and an orthographic projection of the spacing region on the first substrate is overlapped with an orthographic projection of the third electrode part on the first substrate.

5. The detection chip of claim 1, wherein the heating electrode is configured to heat all of the plurality of micro-reaction chambers.

6. The detection chip of claim 5, wherein an area of an orthographic projection of the one continuous electrode on the first substrate is greater than a sum of areas of orthographic projections of the plurality of micro-reaction chambers on the first substrate.

7. The detection chip of claim 1, wherein the one continuous electrode laterally extends beyond edges of the micro-reaction chambers in a direction parallel with a main surface of the first substrate.

8. The detection chip of claim 1, further comprising a plurality of control electrodes, configured to simultaneously apply electrical signals to the heating electrode from different positions.

9. The detection chip of claim 1, further comprising a hydrophilic layer, covering a surface of the micro-cavity defining layer, and lining sidewalls and bottom surfaces of the plurality of micro-reaction chambers.

10. The detection chip of claim 9, further comprising:
    a second substrate, disposed over the first substrate, and the micro-cavity defining layer is disposed in a space between the heating electrode on the first substrate and the second substrate; and
    a hydrophobic layer, disposed on a side of the second substrate facing the micro-cavity defining layer.

11. The detection chip of claim 9, further comprising:
    a hydrophobic layer, covering a portion of the hydrophilic layer in a spacing region between the micro-reaction chambers.

12. A reaction system, comprising a control device and the detection chip according to claim 1,
    wherein the control device is electrically connected to the detection chip, and is configured to apply an electrical signal to drive the heating electrode of the detection chip.

13. A using method of a detection chip, wherein the detection chip comprises:
    a first substrate;
    a micro-cavity defining layer, being on the first substrate and defining a plurality of micro-reaction chambers; and
    a heating electrode, located between the first substrate and the micro-cavity defining layer, and configured to heat the plurality of micro-reaction chambers, wherein an orthographic projection of the plurality of micro-reaction chambers on the first substrate is within an orthographic projection of the heating electrode on the first substrate; and the plurality of micro-reaction chambers comprises a first micro-reaction chamber and a second micro-reaction chamber spaced apart from each other, and the heating electrode continuously extends from a first position corresponding to the first micro-reaction chamber to a second position corresponding to the second micro-reaction chamber;

the heating electrode comprises one continuous electrode, orthographic projections of the plurality of micro-reaction chambers on the first substrate are within an orthographic projection of the one continuous electrode on the first substrate;

wherein the using method comprises:

introducing a reaction system solution into the plurality of micro-reaction chambers of the detection chip through a sample inlet of the detection chip; and driving the heating electrode to heat the plurality of micro-reaction chambers.

14. A detection chip, comprising:
a first substrate;
a micro-cavity defining layer, disposed over the first substrate and defining a plurality of micro-reaction chambers, and comprising a spacing region between the plurality of micro-reaction chambers;
a heating electrode, disposed on the first substrate, and between the first substrate and the micro-cavity defining layer, and configured to heat the plurality of micro-reaction chambers;
wherein orthographic projections of the plurality of micro-reaction chambers on the first substrate and an orthographic projection of the spacing region between the plurality of micro-reaction chambers on the first substrate are both within an orthographic projection of the heating electrode on the first substrate;

an area of the orthographic projection of the heating electrode on the first substrate is greater than a sum of areas of the orthographic projections of the plurality of micro-reaction chambers on the first substrate and an area of the orthographic projection of the spacing region on the first substrate.

15. The detection chip of claim 14, wherein the heating electrode laterally extends beyond edges of the micro-cavity defining layer in a direction parallel with a main surface of the first substrate.

16. The detection chip of claim 14, wherein the heating electrode comprises:
first portions, directly below the micro-reaction chambers; and
a second portion, directly below the spacing region between the micro-reaction chambers, wherein the heating electrode is a continuous electrode in which the first portions and the second portion of the heating electrode are connected to each other.

17. The detection chip of claim 14, further comprising:
a second substrate, disposed over the first substrate, and the micro-cavity defining layer is disposed in a space between the heating electrode on the first substrate and the second substrate;
wherein the heating electrode comprises an extension part laterally extending beyond an edge of the second substrate in a direction parallel with a main surface of the first substrate.

18. The detection chip of claim 17, further comprising:
a control electrode, electrically connected to the extension part of the heating electrode, and configured to apply an electrical signal to the heating electrode.

\* \* \* \* \*